United States Patent [19]

Kahan et al.

[11] 4,162,193

[45] Jul. 24, 1979

[54] ENZYMATIC CLEAVAGE OF N-ACYL-THIENAMYCINS

[75] Inventors: Jean S. Kahan; Frederick M. Kahan, Rahway, N.J.

[73] Assignee: Merck & Co., Inc., Rahway, N.J.

[21] Appl. No.: 825,883

[22] Filed: Aug. 19, 1977

[51] Int. Cl.$^2$ ............................................. C12D 13/06
[52] U.S. Cl. ................................................... 43/121
[58] Field of Search ..................................... 195/29, 30

[56] References Cited

U.S. PATENT DOCUMENTS

| | | | |
|---|---|---|---|
| 3,304,236 | 2/1967 | Nuesch et al. | 195/29 |
| 3,912,589 | 10/1975 | Smith et al. | 195/29 |
| 3,945,888 | 3/1976 | Takahashi et al. | 195/29 |
| 3,950,357 | 4/1976 | Kahan et al. | 195/80 R |
| 3,975,235 | 8/1976 | Niwa et al. | 195/29 |

FOREIGN PATENT DOCUMENTS 939708  4/1963  United Kingdom.

OTHER PUBLICATIONS

Advances in Applied Microbiology, vol. 17, pp. 311–319 (1974).
Journal of Biochemistry, vol. 115, pp. 733–739 (1969).

*Primary Examiner*—Alvin E. Tanenholtz
*Attorney, Agent, or Firm*—Hesna J. Pfeiffer; James A. Arno; Julian S. Levitt

[57] ABSTRACT

A method is disclosed for cleaving N-acyl-thienamycin compounds to yield thienamycin. The new method disclosed herein utilizes enzymes which are penicillin amidohydrolases to treat the starting compounds resulting in the antibiotic thienamycin.

5 Claims, No Drawings

ENZYMATIC CLEAVAGE OF N-ACYL-THIENAMYCINS

BACKGROUND OF THE INVENTION

The enzyme, penicillin amidohydrolase of bacterial or fungal origin is used on an industrial scale to catalyze the hydrolytic removal of the side chain of penicillin to give the nucleus 6-amino penicillanic acid (6-APA). This nucleus is the starting material for the synthesis of broad spectrum penicillins (semi-synthetic) which are prepared by acylation of the amino group.

The International Commission of Enzyme Nomenclature has given the enzyme the systematic name, penicillin amidohydrolase (E.C. 3.5.1.11).

A new antibiotic is thienamycin, (U.S. Pat. No. 3,950,357). The teachings of U.S. Pat. No. 3,950,357 are incorporated herein by reference. N-acyl derivatives of thienamycin are unexpectedly cleaved by penicillin amidohydrolase.

SUMMARY OF THE INVENTION

The present invention provides a new process for conversion of N-acyl-thienamycins to thienamycin.

According to the present invention, N-acylthienamycin, having the following structure:

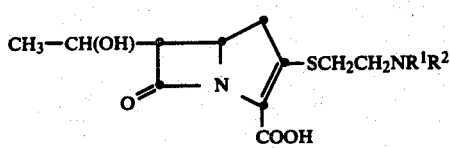

I wherein $R^1$ and $R^2$ are independently selected from the group consisting of hydrogen ($R^1$ and $R^2$ are not both hydrogen) or an acyl group is contacted in an aqueous medium with enzymes which are capable of removing the N-acyl moiety in order to form thienamycin.

Thienamycin has the structure:

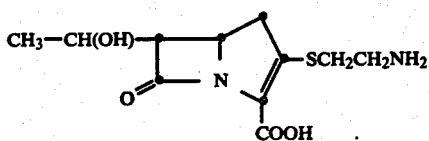

II

Thienamycin is a valuable antibiotic which is active against both gram-positive and gram-negative bacteria.

More particularly, the enzymes utilized to remove the N-acyl moiety are penicillin amidohydrolases.

The preferred compounds of this invention are those wherein $R^1$ is hydrogen and $R^2$ is acyl. By the term "acyl" is meant the aliphatic and aromatic carboxylic acids including derivatives and analogs thereof such as thio analogs wherein the carbonyl oxygen is replaced by sulphur, diacyl radicals wherein $R^1$ and $R^2$ are joined together; as well as the sulphur and phosphorous acyl analogs such as substituted sulfonyl-, sulfinyl-, and sulfenyl-radicals, and substituted P(III) and P(V) radicals such as the substituted phosphorous-, phosphoric-, phosphonous- and phosphonic radicals, respectively. Such acyl radicals of the present invention are further defined below.

DETAILED DESCRIPTION OF THE INVENTION

The N-acyl derivatives may be prepared by any of the techniques well known in the art if the thienamycin has been isolated from the fermentation broth or solution. If the thienamycin has not been isolated from the fermentation broth, then the method of preparing the N-acyl-thienamycin is by reacting the appropriate acyl compound while the thienamycin is still in the broth or solution. Alternatively, the acyl group can be incorporated biosynthetically following supplementation of the fermentation broth with the parent acid or a derivative thereof. These derivatives, by virtue of their increased solubility in organic solvents and additional physical properties, provide alternate and more efficient routes for recovery of the thienamycin nucleus. Once the derivatized thienamycin is recovered from the broth or solution, it can be treated by the methods described in this invention in order to regenerate the thienamycin.

In the generic representation of the compounds of the present invention (I, above), the acyl radical represented by either $R^1$ or $R^2$ can, inter alia, be substituted or unsubstituted aliphatic, aromatic or heterocyclic, araliphatic or heterocylylaliphatic carboxylic acid radical, a substituted or unsubstituted carbamyl radical or a carbothioic acid radical. One group of acyl radicals can be represented by the general formula:

wherein X is O or S and R" represents a straight or branched chain alkyl or alkoxymethylene group containing from 5-10 carbon atoms, aryloxymethylene, typically comprising 6-10 carbon atoms. Such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1-6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, phenoxymethylene, p-hydroxybenzyl, n-amyl, n-heptyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, D-4-N-benzoylamino-4-carboxy-n-butyl, p-aminobenzyl, o-aminobenzyl, m-aminobenzyl, p-dimethylaminobenzyl, 2-ethoxy-1-napthyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 2-phenylvinyl, 2-phenylethynyl, phenyl, o-methoxyphenyl, o-chlorophenyl, o-phenylphenyl, and p-aminomethylbenzyl.

The preferred compounds that can be utilized in this invention that fit the above acyl radical description are phenylacetyl, p-hydroxyphenylacetyl, phenylglycyl, 2-thienylacetyl, phenoxyacetyl, N-propoxyacetyl and iso-butoxyacetyl.

The use of penicillin amidohydrolases to convert penicillins into 6-aminopenicillanic acid (6-APA) is known in the art. However, the use of penicillin amidohydrolases to remove the N-acyl side chains of N-acylated thienamycin is surprising. The process of this invention may be conducted by reacting the starting material of the general formula I with the enzyme extract from a cultured broth, the filtrate or fermentation product of the *Escherichia coli* culture or a powder of the enzyme in an aqueous solution. Alternatively, the enzyme may be immobilized by adsorption or chemical reaction to an insoluble supporting structure such as glass, cellulose or agarose, and used to hydrolyse the N-acylated thienamycin either by contacting it in suspension, or by the percolation of the acylated material through a bed of the immobilized enzyme preparation.

The enzyme is capable of removing N-acyl moietys which were present or produced in fermentation broths as well as those N-acyl groups introduced during isolation of the antibiotic or made by chemical synthesis techniques.

More particularly, the deacylation of N-acylated thienamycin takes place in the presence of an enzyme of the microorganism of the genus *Escherichia coli* which is able to remove the acyl moiety to provide the antibiotic thienamycin.

For the production of the amidohydrolase enzyme by cultivation of the above-mentioned microorganism, there may be used various culture media commonly employed for the cultivation of a microorganism. More specifically, glucose, sucrose, glycerol, starch, oils used for cultivation and the like as a carbon source and peptone, buillion, corn steep liquor, yeast extract, meat extract, fish meal, defatted soybean, wheat embryo and the like as a nitrogen source may be employed. If required, other additives may be employed in combination with the above. It is an advantage but not a necessity to include phenylacetic acid or its salts or derivatives in fermentation media.

As a cultivation method, *Escherichia coli* is usually shaken or agitated under aeration. Cultivation temperature may range from about 23°–27° C. Cultivation period is usually 20–28 hours.

The amidohydrolase contained in the cultured broth or its extract may be utilized in the present process without any further purification. The amidohydrolase enzyme may be precipitated with appropriate solvents, salted out or dialyzed or otherwise purified. It may be used free in solution or immobilized on an appropriate surface.

A method utilized in the present invention is that of utilizing the whole cell amidohydrolase preparation. By this method, after cultivation, the culture is centrifuged to obtain the whole cells for subsequent reaction with the derivatized thienamycin.

The following are given for illustration purposes only and are not to be construed as limiting the scope of the present invention in any way.

EXAMPLE 1

Fifty ml. of 2.5% yeast extract containing 0.08% neutralized (with NaOH) phenylacetic acid in a 250-ml. Erlenmeyer flask is inoculated with a tube of lyophilized culture of MB-2929 (*Escherichia coli* N.C.I.B. 8743). This flask is shaken at 25° C. at 240 rpm for 24 hours. A 35-ml. portion is centrifuged at 7500 rpm for 15 minutes. The supernatant is discarded and the pellet resuspended in 18 ml. of distilled water. The solution is centrifuged at 7500 rpm for 15 minutes. The supernatant is discarded and the pellet taken up in 1 ml. 0.05M potassium phosphate buffer, pH 7.4 to yield a whole cell amidohydrolase preparation which is then stored at 0° C.

The following reaction mixtures are incubated 18 hours at 23° C.

1. A 10-$\mu$l. portion of whole cell amidohydrolase preparation plus 30 $\mu$l. of an approximately 400-$\mu$g./ml. solution of N-phenylacetyl thienamycin.

2. A 10-$\mu$l. portion of 0.05M potassium phosphate buffer, pH 7.4 plus 30 $\mu$l. of an approximately 400 $\mu$g./ml. solution of N-phenylacetyl thienamycin.

3. A 10-$\mu$l. portion of whole cell amidohydrolase preparation plus 30 $\mu$l. of an approximately 1.3-mg/ml. solution of N-(O-formyl)-1-mandeloyl thienamycin.

4. A 10-$\mu$l. portion of 0.05M potassium phosphate buffer, pH 7.4 plus 30 $\mu$l. of an approximately 1.3 mg./ml. solution of N-(O-formyl)-1-mandeloyl thienamycin.

5. A 10-$\mu$l. portion of 0.05M potassium phosphate buffer pH 7.4 plus 30 ml. of a 1-mg./ml. solution of thienamycin.

After the 18 hours of incubation, 1-$\mu$l. aliquots of the reaction mixtures are applied to a cellulose-coated TLC plate, which is developed in EtOH:H$_2$O 70:30. After air drying, the TLC plate is placed on a *Staphylococcus aureus* ATCC 6538P assay plate for five minutes.

The assay plates are prepared as follows: An overnight growth of the assay organism, *Staphylococcus aureus* ATCC 6538P, in nutrient broth plus 0.2% yeast extract is diluted with nutrient broth, plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm. × 22.5 cm. petri plates, and these plates are chilled and held at 4° C. until used (5 days maximum).

The TLC plate is removed and the assay plate incubated overnight at 37° C.

The following bioactive spots are observed:

1. $R_f$ 0.45 and 0.81;
2. $R_f$ 0.82;
3. $R_f$ 0.39 and 0.78;
4. $R_f$ 0.76
5. $R_f$ 0.39–0.45.

The additional bioactive spots present at $R_f$ 0.39 and $R_f$ 0.45 in the enzyme-treated reaction mixtures containing phenylacetyl thienamycin and N-(O-formyl)-1-mandeloyl thienamycin are due to the thienamycin produced by amdohydrolase enzyme reaction. A control containing buffer and enzyme alone produces no bioactive spots.

What is claimed is:

1. A method for the preparation of thienamycin having the structure:

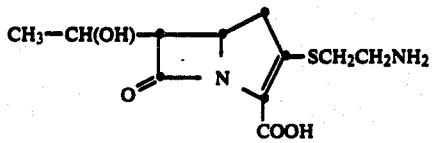

which comprises bringing into contact a compound having the formula:

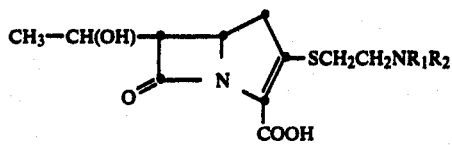

wherein $R_1$ and $R_2$ are independently selected from the group consisting of hydrogen and acyl radical wherein $R_1$ and $R_2$ are not both hydrogen, with a penicillin amidohydrolase, which contact causes the removal of the acyl radical.

2. A process according to claim 1 wherein the acyl radical is represented by the formula:

wherein X is O or S and R" represents straight or branched chain alkyl or alkoxymethylene containing 5–10 carbon atoms; alkyl thio, aryl thio from 6–10 carbon atoms; aryloxymethylene containing 6–10 carbon atoms.

3. A process according to claim 1 wherein the acyl radical is selected from the group consisting of phenylacetyl, p-hydroxyphenylacetyl, phenylglycyl, 2-thienylacetyl, phenoxyacetyl, N-propoxyacetyl and iso-butoxyacetyl.

4. A process according to claim 1 wherein the penicillin amidohydrolase is E.C. 3.5.1.11 from *Escherichia coli*, N.C.I.B. 8743.

5. A process according to claim 4 wherein the reaction is conducted in an aqueous medium.

* * * * *